United States Patent [19]

Gittos et al.

[11] 4,235,778
[45] Nov. 25, 1980

[54] 2-PYRROLIDONE COMPOUNDS AND PROCESSES FOR MAKING SAME

[75] Inventors: Maurice W. Gittos, Strasbourg; Gerard J. Letertre, Souffelweyersheim, both of France

[73] Assignee: Merrell Toraude et Compagnie, Strasbourg, France

[21] Appl. No.: 45,005

[22] Filed: Jun. 4, 1979

Related U.S. Application Data

[62] Division of Ser. No. 873,273, Jan. 30, 1978, Pat. No. 4,178,463.

[51] Int. Cl.³ .............................................. C07D 207/08
[52] U.S. Cl. ................................................. 260/326.45
[58] Field of Search .................................... 260/326.45

[56]  References Cited

U.S. PATENT DOCUMENTS 4,178,463   12/1979   Gittos et al. ................... 260/326.45

*Primary Examiner*—Jose Tovar
*Attorney, Agent, or Firm*—L. Ruth Hattan; Salvatore R. Conte; George W. Rauchfuss, Jr.

[57]  ABSTRACT

Novel compounds of the following general formula are useful in the preparation of 4-aminohex-5-enoic acid and 4-aminohex-5-ynoic acid which are useful pharmacological agents:

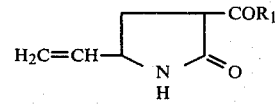

wherein $R_1$ is hydroxy, amino, or tert-butoxy.

4 Claims, No Drawings

2-PYRROLIDONE COMPOUNDS AND PROCESSES FOR MAKING SAME

This is a division of application Ser. No. 873,273 filed Jan. 30, 1978, now U.S. Pat. No. 4,178,463 issued Dec. 12, 1979.

FIELD OF INVENTION

This invention relates to novel 2-pyrrolidone compounds, a process for their preparation and the use of said compounds in the preparation of pharmacologically useful compounds.

SUMMARY OF INVENTION

Compounds of the following general Formula I are novel and useful as chemical intermediates or starting materials for the preparation of pharmacologically useful compounds:

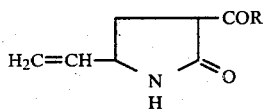

Formula I

In the above general Formula I $R_1$ is hydroxy, amino, or tert-butoxy. Salts of the compounds of general Formula I are also included within the scope of this invention.

DETAILED DESCRIPTION OF INVENTION

Salts of compounds of general Formula I when $R_1$ is hydroxy include those formed with inorganic bases, for example those of alkali metals such as sodium or potassium or alkaline earth metals, such as, calcium or magnesium or organic amines, ethylamine, cyclohexylamine or pyridine.

The compounds of general Formula I are 3-carboxy-5-vinyl-2-pyrrolidone, 3-carboxamido-5-vinyl-2-pyrrolidone, and 3-tert-butoxycarbonyl-5-vinyl-2-pyrrolidone.

The compounds of general Formula I are prepared by reacting a 2-vinylcyclopropane-1,1-dicarboxylic acid derivative of the formula

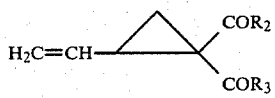

Formula II with ammonia gas in an inert polar solvent at a temperature of about 25° to 150° C. for about 4 to 24 hours. Suitable solvents for the reaction are, for example, formamide, dimethylformamide, N-methylformamide or lower alcohols, such as, methanol, ethanol, n-propanol, isopropanol or n-butanol.

In the above general Formula II each of $R_2$ and $R_3$ are different and represent a straight or branched alkoxy group of from 1 to 4 carbon atoms for example, methoxy, ethoxy, n-propoxy, isopropoxy, n-butoxy or tert-butoxy or $R_2$ and $R_3$ are the same and represent a straight or branched alkoxy group having from 1 to 6 carbon atoms for example, methoxy, ethoxy, n-propoxy, tert-butoxy, neopentoxy or n-hexyloxy or a straight or branched alkenyloxy group having from 2 to 4 carbon atoms for example, 2-propenyloxy, 1-methyl-2-propenyloxy, 2-butenyloxy or vinyloxy or $R_2$ and $R_3$ together represent a lower alkylenedioxo group having the structure

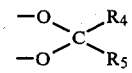

wherein each of $R_4$ and $R_5$ may be the same or different and represents a straight chain alkyl group having from 1 to 4 carbon atoms, that is, methyl, ethyl, n-propyl and n-butyl.

In the ammoniolysis reaction when a compound of general Formula II wherein $R_2$ and $R_3$ together form the group

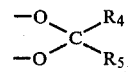

described above the compound of Formula I wherein $R_1$ is hydroxy will be obtained. When a compound of Formula II wherein either or both of $R_2$ and $R_3$ is an alkoxy group containing tertiary branching on the first carbon atom, compounds of Formula I containing the corresponding alkoxy group as the $R_1$ substituent will be obtained. When either or both of $R_2$ and $R_3$ represents an alkenyloxy group or an alkoxy group containing no tertiary branching on the first carbon atom compounds of general Formula I wherein $R_1$ is hydroxy or amino are obtained. It has been found that lower reaction temperatures, that is, temperatures of about 25° to 60° C. favor formation of compounds of Formula I wherein $R_1$ is hydroxy whereas higher temperatures, that is, from about 60° to 150° C., favor formation of compounds of Formula I wherein $R_1$ is amino.

The compounds of general Formula II wherein $R_2$ and $R_3$ are the same or different and represent a straight or branched alkoxy group of from 1 to 4 carbon atoms or $R_2$ and $R_3$ are the same and represent a straight or branched alkoxy group having from 1 to 6 carbon atoms or a straight or branched alkenyloxy group having from 2 to 4 carbon atoms are known in the art or may be prepared by procedures generally known in the art. For example, said compounds of Formula II may be prepared by condensation of an appropriate malonate of the formula

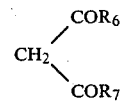

Formula III with 1,4-dibromo-2-butene as generally described by R. W. Kierstead et al., J. Chem. Soc. 1952, 3610–16. In the above general Formula III $R_6$ and $R_7$ are the same or different and represent a straight or branched alkoxy group of from 1 to 4 carbon atoms or $R_6$ and $R_7$ are the same and represent a straight or branched alkoxy group having from 1 to 6 carbon atoms or a straight or branched alkenyloxy group having from 2 to 4 carbon atoms.

The compounds of general Formula II wherein $R_2$ and $R_3$ together represent a lower alkylenedioxo group of the structure

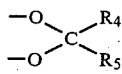

as defined hereinabove are known in the art or may be prepared by treating a mixture of 2-vinylcyclopropane-1,1-dicarboxylic acid and a vinyl acetate derivative of the formula

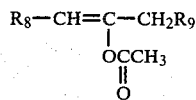

the isomer thereof having the formula

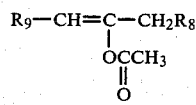

or a mixture of the isomers, wherein each of $R_8$ and $R_9$ is hydrogen or a straight chain alkyl having from 1 to 3 carbon atoms, with concentrated sulfuric acid as illustrated more fully in the specific examples below.

The compounds of general Formula I are useful in the preparation of 4-aminohex-5-enoic acid and 4-aminohex-5-ynoic acid having the following respective structures:

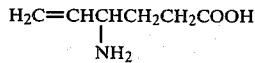 Formula VI

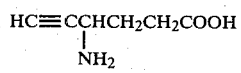 Formula VII

The compounds of Formulas VI and VII are irreversible inhibitors of γ-aminobutyric acid transaminase rendering said compounds useful in the treatment of disorders of the central nervous system function as reported in U.S. Pat. Nos. 3,960,927 issued June 1, 1976 and 3,959,356 issued May 25, 1976.

In preparing the compound of Formula VI, or a salt thereof, a compound of Formula I is treated with an excess of a strong acid at about 100° to 150° C. for about 2 to 24 hours. Alternatively, a compound of Formula I may be treated with an excess of a strong base followed by treatment with an excess of strong acid as described above. Suitable strong acids are for example, hydrochloric, hydrobromic, methanesulfonic, toluenesulfonic or trifluoroacetic acids. Suitable strong bases are, for example, sodium hydroxide or potassium hydroxide. When the free base of the compound of Formula VI is desired the thus formed acid salt is treated with base for example, sodium hydroxide or potassium hydroxide, or applied to an acid ion exchange resin.

In preparing the compound of Formula VII, or a salt thereof, a compound of Formula I is treated with a strong base in a lower alcohol solvent, such as methanol, ethanol or isopropanol, at a temperature of about 20° C. to the reflux temperature of the solvent for about 6 to 24 hours when $R_1$ is amino. When $R_1$ in the compound of Formula I is hydroxy or tertiary butoxy the above-described treatment with base is unnecessary. The 3-carboxy-5-vinyl-2-pyrrolidone compound or its tertiary butyl ester is then decarboxylated. Decarboxylation may be achieved by several methods generally known in the art. For example, the 3-carboxy derivative and/or its tertiary butyl ester may be treated with anhydrous acetic acid for about 6 to 24 hours at a temperature of about 110° to 120° C. Also, the 3-carboxy compound may be heated to a temperature exceeding the melting point of said compound for about 4 to 20 hours to affect the decarboxylation. Heating the 3-carboxy compound with quinoline to about 120° to 180° C. for about 4 to 12 hours will also achieve decarboxylation. Decarboxylation may also be achieved by converting the 3-carboxy compound to the corresponding barium or calcium salt and heating said salt to 120° to 160° C. for about 4 to 12 hours. The preferred method is treatment with anhydrous acetic acid.

The thus formed 4-vinyl-2-pyrrolidone derivative is treated in a chlorinated hydrocarbon solvent, such as, chloroform, methylene chloride, chlorobenzene or carbon tetrachloride or acetic acid, with bromine at about 0° to 30° C. with stirring for about 4 to 24 hours. Equimolar amounts of bromine and 4-vinyl-2-pyrrolidone are used. The thus formed dibromo compound in an ether solvent, such as, diethyl ether, tetrahydrofuran or p-dioxane or liquid ammonia is treated with a strong base then stirred about 15 to 40 hours at a temperature of about −80° to 120° C. followed by quenching with water. Suitable strong bases are, for example, alkyl lithium, such as, butyllithium, or phenyllithium, lithium di-alkylamide, such as, lithium diisopropylamide, lithium tetramethylpiperidide, lithium amide, sodium amide, potassium amide or potassium tertiary butoxide. A preferred method is the use of potassium tertiary butoxide in tetrahydrofuran at temperatures ranging from −80° to −40° C. The thus formed 5-acetylene-2-pyrrolidone is hydrolyzed with acid, for example, by treatment with aqueous acid, such as, hydrochloric, hydrobromic, methanesulfonic, toluenesulfonic or trifluoroacetic acids, at reflux temperature for about 2 to 6 hours. The thus formed acid salt of the compound of Formula VII may be converted to the free base by treatment with base, such as, sodium hydroxide or potassium hydroxide or by application to an acid ion exchange resin.

The above described processes for preparing the compounds of Formulas VI and VII offer certain advantages over methods known in the art, such as, increased yields of product and fewer steps. Also the above described processes are more economical and safer than known prior art methods.

Also when preparing a compound of Formula I from a cyclopropane derivative of Formula II as described hereinabove said compound of Formula I need not necessarily be isolated for conversion to either the compound of Formula VI or VII.

The following specific examples further illustrate the invention.

EXAMPLE 1

6,6-Dimethyl-2-vinyl-5,7-dioxaspiro(2,5)octane-4,8-dione

To a mixture of 31.2 g of 2-vinylcyclopropane-1,1-dicarboxylic acid and 26 g of isopropenyl acetate cooled in an ice-water bath is added 3.6 g of concentrated sulfuric acid dropwise over half an hour. The reaction mixture is stirred for an additional hour at room temperature after which the solution is diluted with ether and extracted with 5% aqueous sodium bicarbonate. The organic layer is dried over magnesium sulfate. Evaporation of the volatiles leaves a residue which is crystallized from hexane-benzene (about 5:1) to give 6,6-dimethyl-2-vinyl-5,7-spiro(2.5)octane-4,8-dione M.P. 51°-53° C.

EXAMPLE 2

1,1-Bis-ethoxycarbonyl-2-vinylcyclopropane

To a solution of 18.4 g (2 equivalents) in 300 ml of anhydrous ethanol is added rapidly 164 g (1 equivalent) of diethyl malonate. 1,4-Dichloro-2-butene (98% mixture of cis and trans, Aldrich) (50 g, 1 equivalent) is slowly added to the warm, stirred suspension of the diethyl sodio malonate during 15 minutes after which the mixture is refluxed for 3 hours. Upon cooling, the mixture is poured into 1.2 liters of water and an oil isolated by ether extraction. The ether extract is dried over magnesium sulfate and distilled to give 1,1-bis-ethoxycarbonyl-2-vinylcyclopropane, B.P. 108°-116° C./14 mm.

EXAMPLE 3

3-Carboxamido-5-vinyl-2-pyrrolidone

Ammonia gas is bubbled through a solution of 3 g of 1,1-bis-ethoxycarbonyl-2-vinylcyclopropane in 20 ml of formamide at 120°-130° C. during 16 hours. The solution is concentrated under high vacuum, the resulting residue dissolved in the minimum amount of water and the solution extracted with ether. Crystals form from the aqueous solution an are filtered off and recrystallized from methanol to give 3-carboxamido-5-vinyl-2-pyrrolidone, M.P. 215° C.

EXAMPLE 4

3-Carboxy-5-vinyl-2-pyrrolidone

Ammonia gas is bubbled through a stirred solution of 5 g of 6,6-dimethyl-5-vinyl-5,7-dioxaspiro(2,5)octane-4,8-dione in 35 ml of dimethyl formamide. The temperature of the mixture increased from 20° to 55° C. during 30 minutes. The mixture is stirred for 3.5 hours during which time the temperature returned to 20° C. The mixture is concentrated under high vacuum. The resulting residue is treated with dilute (5%) hydrochloric acid and extracted with ether. Evaporation of the dried (over magnesium sulfate) ether extract gives 3-carboxy-5-vinyl-2-pyrrolidone or 2-oxo-5-vinyl-3-pyrrolidinyl-carboxylic acid. M.P. 143°-4° C.

EXAMPLE 5

4-Aminohex-5-enoic acid

A mixture of 1.5 g of 3-carboxamido-5-vinyl-2-pyrrolidone, 20 ml of concentrated hydrochloric acid and 10 ml of glacial acetic acid is refluxed for 16 hours after which the solution is evaporated to dryness under reduced pressure. The resulting residue is dissolved in the minimum quantity of water. The aqueous solution is extracted with ether, treated with charcoal and neutralized using 2 M aqueous ammonia. The neutral solution is applied to an Amberlite I.R. 120 column, and the product eluted with 2 M aqueous ammonia. The ammonia solution is evaporated leaving a residue which is recrystallized from aqueous acetone to give 4-aminohex-5-enoic acid, M.P. 208°-210° C.

EXAMPLE 6

4-Aminohex-5-enoic acid

Ammonia gas is bubbled through a solution of 30 g of 1,1-bis-ethoxycarbonyl-2-vinylcyclopropane in 150 ml of formamide at 120°-125° C. for 16 hours. The solution is concentrated under high vacuum, and the resulting residue is dissolved in a mixture of 75 ml of glacial acetic acid and 150 ml of concentrated hydrochloric acid. The solution is refluxed for 16 hours, evaporated to dryness under reduced pressure, and the residue treated with 10 ml of 5 N ammonium hydroxide. The ammonium hydroxide solution is evaporated to dryness, and the residue stirred with 200 ml of warm glacial acetic acid. The solid is filtered off, the acetic acid evaporated under reduced pressure, and the residue is dissolved in the minimum quantity of water. The solution is treated with charcoal and then with acetone until 4-aminohex-5-enoic acid crystallizes, M.P. 208°-210° C.

EXAMPLE 7

4-Aminohex-5-ynoic Acid

To a solution of 184 mg (0.008 mole) of sodium in 50 ml of absolute ethanol is added 1 g (0.0065 mole) of 3-carboxamido-5-vinyl-2-pyrrolidone. The mixture is refluxed for 16 hours then evaporated to dryness. The residue is dissolved in water and the solution is neutralized by the addition of dilute hydrochloric acid. The solution is passed through an IR 120 exchange resin and the eluate evaporated to dryness to give 3-carboxy-5-vinyl-2-pyrrolidone as a viscous oil. A solution of 0.78 g of the viscous oil in glacial acetic acid is refluxed for 16 hours. Evaporation of the solution to dryness gives 5-vinyl-2-pyrrolidone. To a stirred solution of 8.88 g (0.08 mole) of 5-vinyl-2-pyrrolidone in 50 ml of carbon tetrachloride at 25° C. is added slowly a solution of 12.8 g (0.08 mole) of bromine in 20 ml of carbon tetrachloride. The mixture is stirred until the bromine color disappears then evaporated to dryness under reduced pressure using a water bath at 40° C. The resulting residue is recrystallized from ethanol to give 5-(1,2-dibromoethyl)-2-pyrrolidone, 2.5 g of which is added to a solution of 1.28 g (6 equivalents) of sodium in 100 ml of liquid ammonia. The mixture is placed in a stainless steel pressure vessel for 2 days at 25° C., after which 1.51 g of ammonium chloride is added. The ammonia is allowed to evaporate in a nitrogen atmosphere. The residue is treated with 120 ml of 3 M hydrochloric acid and refluxed for 16 hours then evaporated to dryness. The residue is purified by using an IR 120 resin column, and the product crystallized from aqueous alcohol to give 4-aminohex-5-ynoic acid, M.P. 240° C.

Similarly in the above procedure the dibromo derivative may be treated with potassium tertiary butoxide in tetrahydrofuran for 30 hours at −60° C. followed by acid hydrolysis and purification to give the product.

We claim:
1. A compound of the formula

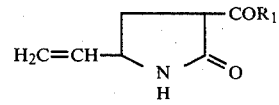

wherein $R_1$ is hydroxy, amino, or tertiary-butoxy, and the alkali metal, alkaline earth metal and organic amine salts thereof when $R_1$ is hydroxy.

2. A compound of claim 1 wherein $R_1$ is hydroxy.
3. A compound of claim 1 wherein $R_1$ is amino.
4. A process for the preparation of a compound of claim 1 which comprises reacting a 2-vinylcyclopropane-1,1-dicarboxylic acid derivative of the formula

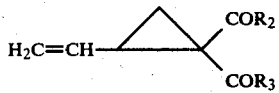

with ammonia gas in an appropriate inert polar solvent at a temperature of about 25° to 150° C. for about 4 to 24 hours wherein each of $R_2$ and $R_3$ are different and represent a straight or branched alkoxy group of from 1 to 4 carbon atoms, or $R_2$ and $R_3$ are the same and represent a straight or branched alkoxy group having from 1 to 6 carbon atoms or a straight or branched alkenyloxy group having from 2 to 4 carbon atoms or $R_2$ and $R_3$ taken together form a lower alkylenedioxo group of the structure

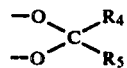

wherein each of $R_4$ and $R_5$ may be the same or different and represents a straight chain alkyl group having from 1 to 4 carbon atoms.

* * * * *